United States Patent [19]

Terra et al.

[11] Patent Number: 4,649,277
[45] Date of Patent: Mar. 10, 1987

[54] MULTIPURPOSE APPARATUS FOR NORMAL OR TOMOGRAPHIC INVESTIGATIONS BY MEANS OF A GAMMA CAMERA

[75] Inventors: Luigi Terra, Milano; Edoardo Sada, Cernobbio; Sergio Colombo, Milano, all of Italy

[73] Assignee: S.E.L.O. Societa Elettronica Lombarda S.p.A., Sesto San Giovanni, Italy

[21] Appl. No.: 665,069

[22] Filed: Oct. 26, 1984

[30] Foreign Application Priority Data

Oct. 27, 1983 [IT] Italy ............................... 23481 A/83

[51] Int. Cl.$^4$ ............................................. G01T 1/166
[52] U.S. Cl. ................................................ 250/363 S
[58] Field of Search .................. 250/363 SB, 363 SC, 250/363 SF, 363 SR, 491.1; 378/117

[56] References Cited

U.S. PATENT DOCUMENTS

| 2,781,454 | 2/1957 | Green et al. | 378/117 |
| 3,852,601 | 12/1974 | Casale | 250/363 SF |
| 4,011,453 | 3/1977 | Delaby | 250/363 SF |
| 4,445,035 | 4/1984 | Veyama | 250/363 SB |
| 4,503,331 | 3/1985 | Kovacs, Jr. et al. | 250/363 SB |

Primary Examiner—Carolyn E. Fields
Attorney, Agent, or Firm—Charles E. Brown; Charles A. Brown

[57] ABSTRACT

A multipurpose apparatus for making normal or tomographic investigations by means of a gamma camera. The apparatus comprises an image detector head mounted on a gantry supported by a column running on guides, which detector head is set in motion in a plane determined by said guides and said column to describe a closed curve trajectory about a supported bed on which the patient is accommodated. The detector head can also rotate about its own support axis, such rotation being such as to allow the head to maintain the detection surface at all times tangential to said trajectory.

15 Claims, 6 Drawing Figures

MULTIPURPOSE APPARATUS FOR NORMAL OR TOMOGRAPHIC INVESTIGATIONS BY MEANS OF A GAMMA CAMERA

The present invention relates to an apparatus for investigations in the field of nuclear medicine by means of the use of at least on gamma camera mounted on a gantry supported by a column which translates on guides in a manner parallel to the patient's bed. The gamma camera or image detector head also describes a combined movement of translation and rotation variable according to a sinusoidal law when the patient is placed in a plane which remains horizontal but with the aixs of the body perpendicular to the translation direction of the column.

Apparatuses for tomography are known, as for example the apparatus described in U.S. Pat. No. 4,220,861, which comprise a base-frame which rotatingly supports at its periphery a horizontal-axis discoid body on which there is in turn radially moveable an articulated support of a detector head, the discoid body featuring a central bore adapted to permit the axial passage of the body of the patient placed on a sliding stretcher-type bed.

The contruction of such apparatuses entails problems which cannot be readily overcome, first and foremost as regards the sizing of the different components. Such apparatuses in fact call for a structure able to support in a stable and vibration free manner a somewhat heavy gamma camera which moves along a circumference about the patient so as to make radial investigations of the patient with movements requiring a certain precision.

Furthermore, the weight of the detector head requires that is support and base-frame be sized to provide appropriate sturdiness, and are thus heavy.

The apparatuses have to be capable of universal use, i.e. have to be able also to detect images by normal technique, that is to say with the gamma camera stationary; this fact involves very considerably kinematic complexity.

Another and not negligible problem is the safety both of the patient and the detector components. The heavy detector head is moved according to circumferences (or ellipses) of variable radius (or parameters) in the immediate vicinity of the patient's body and head, and any error of trajectory or machine breakdown can give rise to dangerous situations.

The detector head positioning mechanism—again in the event of error or malfunctioning—can strike against the patient or the bed and thus be damaged; in such case the economic detriment is in most cases extensive. Finally, because of their heavy and complicated structure, the costs of the apparatuses are considerably higher than those of a conventional gamma camera.

The object of the present invention is to provide a solution to the aforesaid problems by embodying an apparatus of maximum versatility, as uncomplicated as possible, of limited bulk and weight and such as to guarantee dependability and safety and, at the same time, is less costly than the apparatuses now available.

To attain this object the present invention embodies a multipurpose apparatus for normal and tomographic investigations made by means of a gamma camera, characterized in that is comprises a column moveable with respect to the floor, or to a horizontal plane, on guides parallel to a patient's bed, the column supporting a detector head which is moveable both according to the vertical extension of the column and according to the support axis of the detector head, provision being made for drive means for the three movements and control means for coordinating the resulting movement of the detector head in a plane essentially determined by the guides and the column according to a circular trajectory described about a second bed perpendicular to the determined plane.

The characteristics and particular features of an apparatus embodied according to the present invention will be more fully understood from the following description referred to the attached schematic drawings, in which.

Figure 1:
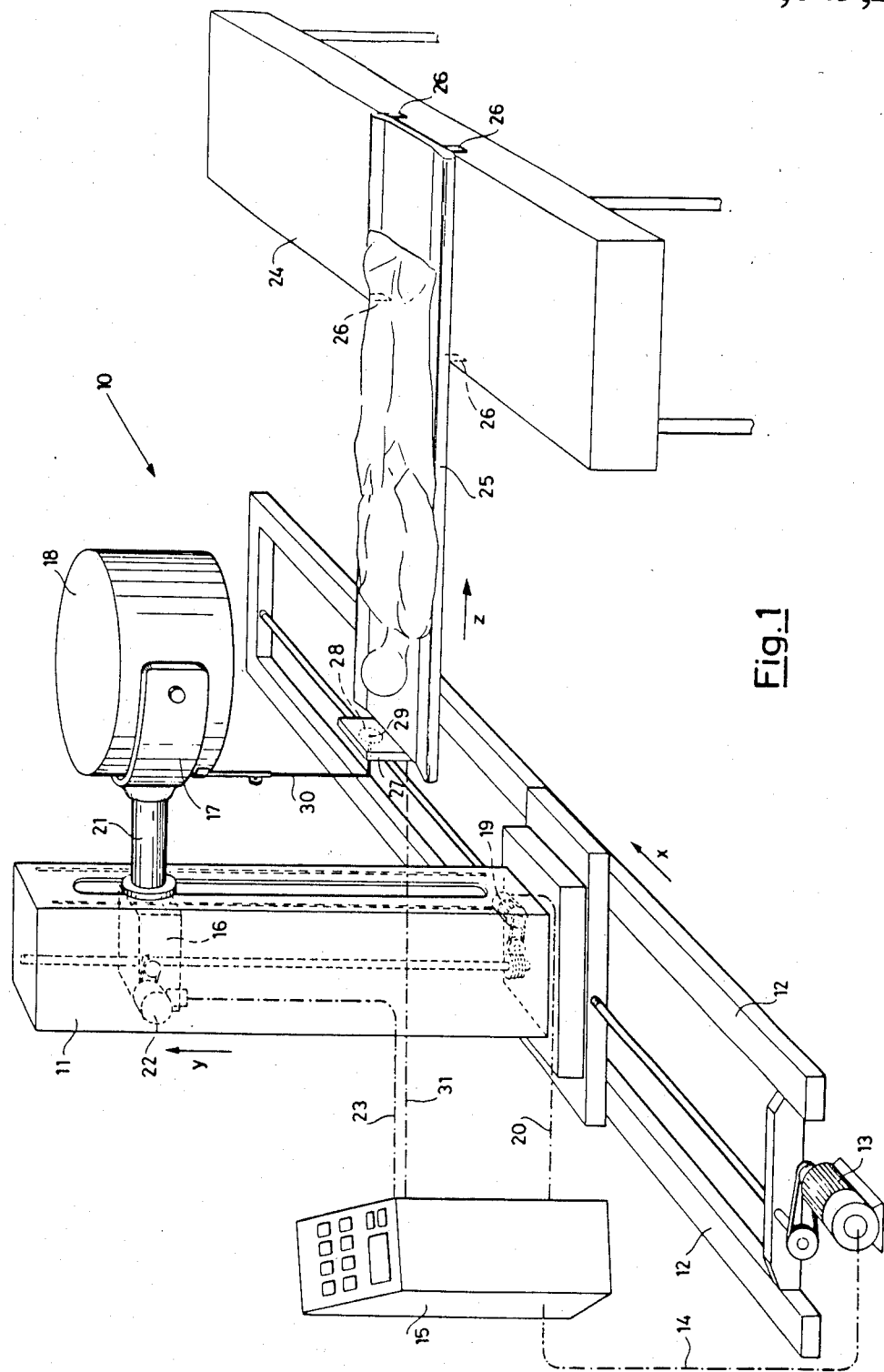
FIG. 1 is a schematic perspective view of an apparatus according to the invention.
Figure 2:
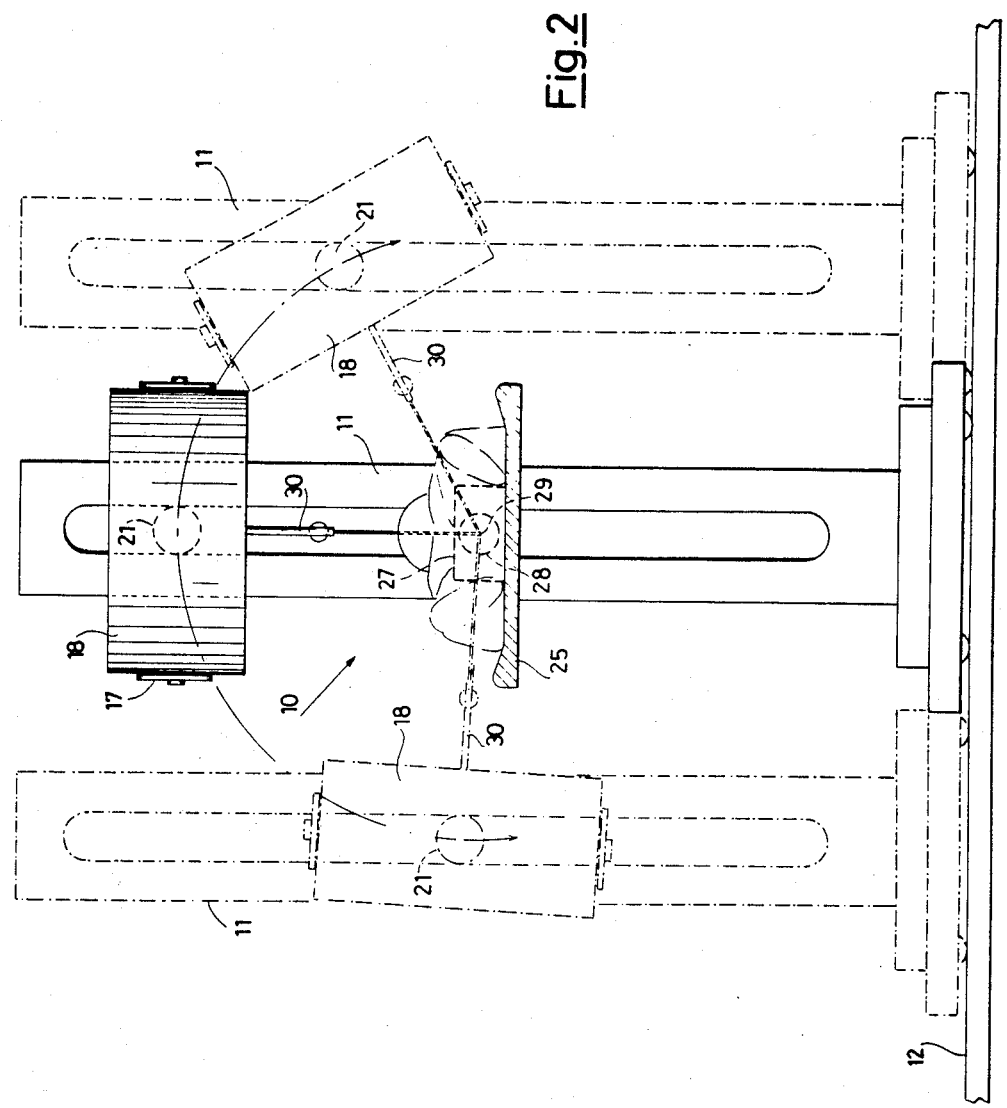
FIG. 2 is a partial front elevation of the apparatus of FIG. 1 with some operational position shown by dotted and dashed lines.
Figure 3:
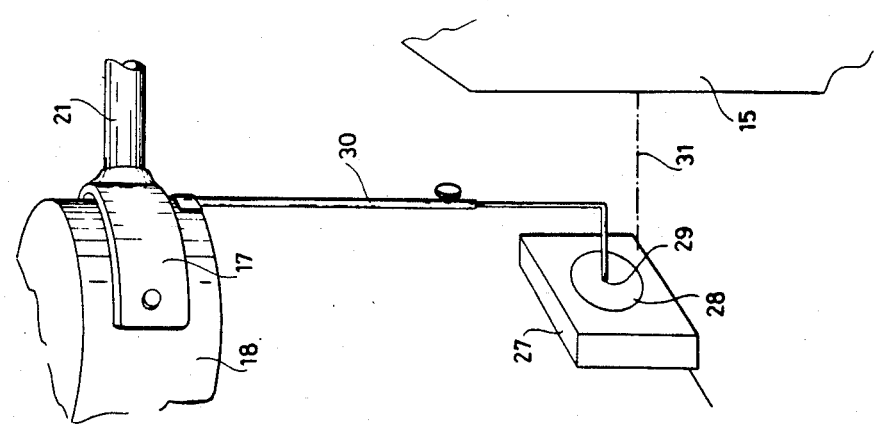
FIG. 3 is an enlarged view of a particular of the image detector head and of a safety device.

With reference to the drawings, a multipurpose apparatus for gamma camera investigations according to the invention, indicated overall by the numeral 10, essentially comprises a column 11 moveable an axis x on guides 12 resting on the floor and moved in known manner by drive means 13 connected by a first line 14 to a computerized electronic command and control unit 15.

A slide 16, freely moveable in conformity with the axis y within said column 11, carries in cantilever-fashion a fork 17 supporting an image detector-head 18, and is moved in the y direction by drive means 19 connected by a second line 20 to the command unit 15.

A shaft 21 bearing the fork 17 controls the rotation of the detector head 18 in the plane xy by drive means 22 which are connected by a third line 23 to the command unit 15.

The drive means and drive transmission devices can be of the screw/nut screw type, or worm screw/helical gear type or can consist of any known device which enables deviations and movements of very considerably precision to be made and which does not permit of reversibility in the event of breakdown or malfunctioning.

A bed 24 of known type is positioned parallel to the direction x of movement of the column 11 and, when positioned in conformity with the axis z, is pre-set to receive and support a rigid stretcher-type supportable bed 25 by means of hooks 26 provided for the purpose; the stretcher type supportable bed 25 is adapted to receive a patient with the axis of the body coincident with or parallel to the axis z.

The opposite end of the stretcher-type bed 25 carries a safety device 27 featuring a circular area 28 sensitive to the presence of an extremity 29 of a rod 30 which is rigidly secured to the detector-head 18 but is adjustable in length so as to cause different rotation radii which can be set in advance at will.

The device 27 is connected by a connection 31 provided for the purpose to the command unit 15 and more particularly to the drive means actuators for immediately stopping the drive means.

An apparatus formed according to the present invention operates as follows: if it is wished to make a normal investigation by a series of imagings over the whole body of the patient by simply moving the detector head 18 along the axis x, the bed 24 is brought parallel to the guides 12 and below the level of the detector head 18. The normal actuation of the drive means 13 and 19 enables the aforesaid nuclear medicine investigation to be performed in a known manner.

If it is wished to make a tomographic investigation, radial views of the patient are necessary. The procedure is in such case as follows: the bed 24 is positioned so as to be in parallel with the raceways 12 of the column 11 and a stretcher-type supportable bed 25 is secured by means of hooks 26 to the bed 24 in a position perpendicular to the previous position, i.e. in conformity with the axis z.

The stretcher-type bed 25 carries at its free end and in overhung manner the safety device 27 in such a way that it will interact with the rod 30 positioned solidly with the detector head 18.

When the apparatus 10 has been arranged as described above, the required investigation can be made. For this purpose the detector head 18 must move with a circular trajectory in the plane xy about the patient, who is positioned in conformity with the axis z, the surface of the detector-head being kept permanently at a tangent to said trajectory, i.e. premanently facing in the direction of the patient.

This is achieved by the compositions of the two movements conforming to the axes x and y, having equations:

$$x = A \cos \omega t$$

$$y = B \sin \omega t$$

where $A = B = R$ and t represents the phase angle.

The circular movement thus brought about is simply a very particular case of a motion resulting from two sinusoidal movements of the same period which take place on straight lines x, y perpendicular to each other, and about the same point.

The more general case has two component motions:

$$x = A_x \cos(\omega t + \phi_x)$$

$$x = A_y \cos(\omega t + \phi_y)$$

which can perform elliptical trajectories which are the best and most suitable trajectories for an investigation of the type in question, in that the patient is thus at an almost constant distance from the detector-head.

To such end the motors 13, 19 and 22 are connected by the command lines 14, 20 and 23 to the central unit 15 in which appropriate electronic circuits, optionally with microprocessors, regulate their actuation. Control means featuring a microprocessor are used to control angular rotation velocity.

The motors are actuated only when, in the patient imaging starting position, the end 29 of the rod 30 is at the centre of the circular area 28 of the safety device 27.

In this way the lengthwise regulation of the rod 30 enables the rotation radius of the detector-head 18 to be set about the axis z of the patient.

During the movement of the detector head 18 in the plane xy, any circular trajectory errors cause the end 29 of the rod 39 to depart from the center of the area 28.

The safety device 27 arrests the movements of the different motors as soon as the end 29 of the rod 39 reaches the periphery of the area 28, thus ensuring the safety of the patient and the intactness of the apparatus.

Said control units can comprise devices with redundant units, for example in duplicate, devices for delecting deviations exceeding the pre-established deviation and other similar devices which also arrest the motors when the alarms provided for are given.

A wholly analogous device can be used when the trajectory of the detector head is elliptical, for example for checking that the distance between a fixed point on the head, and thus on the ellipse, and the foci is constant.

This check can for example be made by means of a small cable locked at its ends in the foci of the ellipse in question and passing over a sheave restrained to the detector head and spanning the said ellipse point by point, said cable being provided with a transducer which measures for example the length or tension and signals any variations therein.

Importance attaches to the fact that an apparatus embodied according to the invention, though preserving an apparent structure as found in the apparatuses known as "Total Body" apparatuses, also enables tomographic investigations to be made with the simple aid of a supportable stretcher-type bed.

The second bed is normally hooked to the conventional support bed, moved to a position parallel to the basic position, and can for example be wholly or partly made of carbon fibre.

It is also possible to employ a stretcher-type bed independently of the support bed, though this is clearly less advantageous from the standpoint of cost and also of bulk.

The fork 17 is longer than that of conventional apparatuses, and this in order to allow operations with the detector head 18 to be performed on at least half the patient's body.

The drive means 22 for rotating the shaft of the fork 17 is correlated with the movements conforming to the axes x and y so as to keep the detection surface permanently at a tangent to the trajectory about the patient's body.

Figure 4:
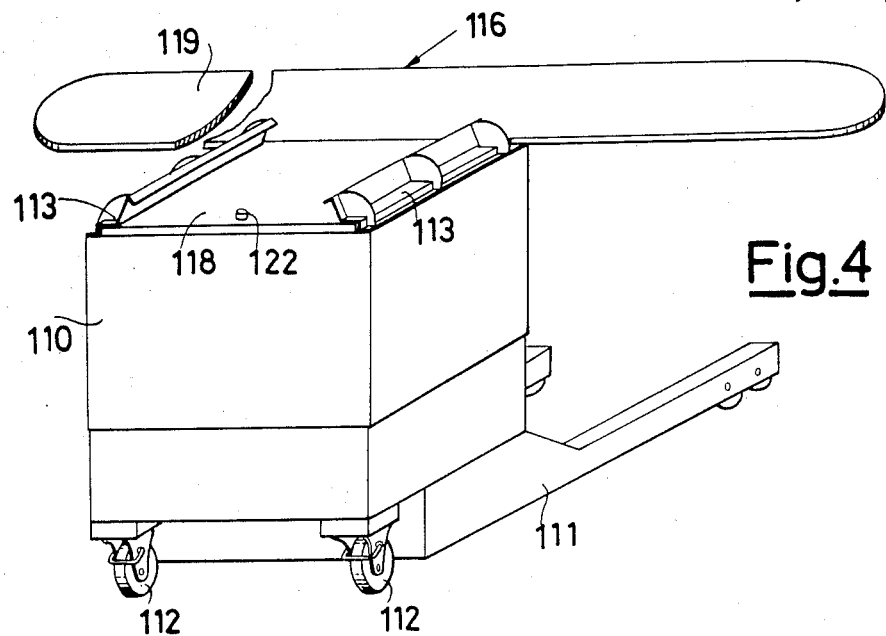
FIG. 4 is a perspective view showing an improved bed pre-set for the making of a normal investigation.
Figure 5:
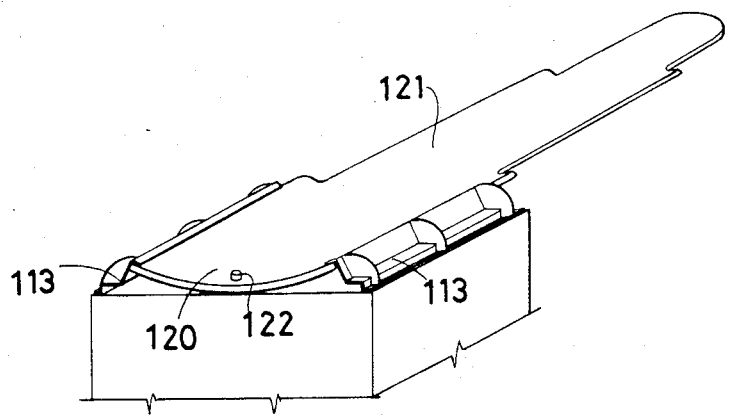
FIG. 5 is a particular of the same bed as per FIG. 4 pre-set for the making of a tomographic investigation.
Figure 6:
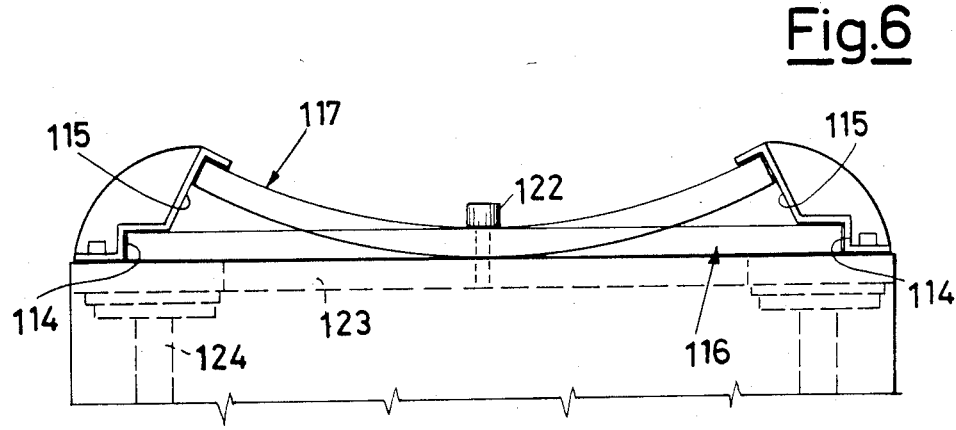
FIG. 6 is a vertical sectional view of said bed.

The bed shown in FIGS. 4–6 of the attached drawings can also be used to advantage in combination with the apparatus according to the invention.

With references to said FIGS. 4–6 the bed in question is structurally composed of a telescopic bearing column 110 mounted eccentrically on a trolley with arms 111 extending in the form of a "U" and provided with wheels at their free end, with which a pair of wheels 112 secured directly to the column 110 cooperate.

According to one characteristic of the present invention, there are fixed to the sides of the upper surface of the column 110 a pair of opposed longitudinal guides 113, for example made of metal, shaped so as to have two sections 114, 115 adapted to receive, respectively, a flat table 116, for nromal investigations, and a curved table 117 for tomographic investigations.

As FIG. 4 of the drawings clearly shows, the flat table 116 is essentially "T"-shaped, with an area 118 for attachment to the guides 113 and with an area 119, jutting out from the column 110, intended to accomodate the patient.

The table 117 (FIG. 5) has a curved cross-section, while it is longitudinally rectilinear with an area 120 for attachment to the guides 113 and with an area 121 jutting out from the column 111 and intended to accomodate the patient.

The longitudinal restraint of both the tables 116, 117 is by means of pins 122, as shown in FIG. 6.

As stated hitherto, according to a further characteristic of the invention, the column 110 is telescopic, so that the upper surface 123 can be adjusted in height, thus allowing the patient to climb on without difficulty and also to be taken to the height required for a normal or a tomographic investigation.

The mechanism controlling the movement of the upper part of the telescopic column with respect to the lower part fixed to the trolley is not here shown in detail, in that it can be of any appropriate type, either manually or motor operated.

The mechanism, for examples, can comprise between the fixed and moveable parts of the column four threaded screws 124 with relative nut screws rotated by a wheel through the agency of a central bevel wheel pair and a chain transmission.

Thus to one rotation of the wheel there will correspond one simultaneous axial translation of all the screws and a movement, either upwards or downwards depending on the rotation direction, of the upper part of the column carrying the surface 123.

What has been described herein with reference to the drawings highlights the flexibility and convenience of use of the bed embodied according to the invention which, pre-set as shown in FIG. 4, serves for normal investigations of nuclear medicine and, when arranged as shown in FIG. 5, for tomographic investigations.

The bearing structure for the projecting tables are particularly noteworthy in that the structure is capsize-proof owing to the "U"-shaped trolley and the eccentric disposition of the column, and can be brought near as required to the apparatus on which the gamma camera is mounted.

We claim:

1. A multipurpose apparatus for normal or tomographic investigations with a gamma camera of a patient laying in a patient's bed, said apparatus comprising guides positioned parallel to the patient's bed in a horizontal plane, a vertically extensible column movable with respect to said horizontal plane, said column having means supporting a detector head for rotation about a horizontal support axis, said detector head being movable both according to the vertical extension of the head on said column and according to the rotation about said support axis, three separate drive means for three movements including a first drive means for adjusting said column horizontally on said guides, second drive means for vertically adjusting said detector head on said column, and third drive means for rotating said detector head about said support axis, a second bed, and control means for coordinating said three movements to provide movement of said detector head in a plane essentially determined by said guides and said column according to a curved trajectory described about said second bed, said second bed being perpendicular to said determined plane.

2. An apparatus according to claim 1, characterized in that said second bed is provided with hook means for restraining said second bed in cantilever fashion to said patient's bed which is in a position parallel to said guides.

3. An apparatus according to claim 1, characterized in that said detector head has a surface which is maintained, during said rotation of said detector head about an axis, constantly at a tangent to a closed curve described by said curved trajectory.

4. An apparatus according to claim 1, characterized in that said curved trajectory is a circle having an axis coincident with or parallel to an axis of a patient's body being investigated.

5. An apparatus according to claim 1, characterized in that said curved trajectory is an ellipse in a plane perpendicular to an axis of a body of a patient being investigated.

6. An apparatus according to claim 1, characterized in that the position of the center of said curved trajectory, the point-by-point distance of said curved trajectory from said center, the angular rotation velocity, the tangency of a detector surface of said detector head to said curved trajectory are assured by said control means, said control means including a microprocessor.

7. An apparatus according to claim 1, characterized in that between said second bed and said detector head are detection means for point-by-point detection of the position of said detector head along said curved trajectory relative to said second bed.

8. An apparatus according to claim 7, characterized in that said detection means are operatively connected to said three drive means for at once arresting said drive means in the absence of correct trajectory.

9. An apparatus according to claim 7, characterized in that said detection means includes a safety device mounted on said second bed and having a sensitive area, and a rod adjustable in length and fixed to said detector head, said rod having one end in said sensitive area.

10. An apparatus according to claim 1, characterized in that the rotation movement of said detector head takes place in a plane containing the axis of said detector head and is effected by moving said detector head in conformity with two rectilinear orthogonal movements variable according to sinusoidal law in a plane formed by said guides and said column.

11. An apparatus according to claim 1, characterized in that said patient's bed comprises a trolley on which is eccentrically mounted a column provided at its top with means for selectively removably securing a first "T"-shaped table for the making of normal investigations or a second rectilinear table for the making of tomographic investigations, both of said tables extending horizontally from said column.

12. An apparatus according to claim 11, characterized in that said trolley is supported on wheels or casters at least one pair of which is secured in proximity to said column and at least another pair of which is secured to ends of "U"-shaped arms of said trolley.

13. An apparatus according to claim 11, characterized in that said securing means include a pair of opposed longitudinal guides shaped so as to have two sections for receiving said first table and said second table respectively.

14. An apparatus according to claim 11, characterized in that pin means for preventing longitudinal movement of said tables within said guides cooperate with said securing means.

15. An apparatus according to claim 11, characterized in that said column is telescopic.

* * * * *